United States Patent [19]

Iwase et al.

[11] Patent Number: 5,764,356
[45] Date of Patent: Jun. 9, 1998

[54] TRACE LIQUID DETECTING AND ANALYZING DEVICE

[75] Inventors: Kenichi Iwase; Hajime Takeuchi; Yuuki Umehara, all of Kyoto; Takayuki Taguchi, Sanda; Shigeru Fujioka, Tokyo; Tadao Yamaguchi, Sanda, all of Japan

[73] Assignees: Nihon Medi-Physics Co., Ltd., Hyogo-Ken; Teramecs Co., Ltd., Osaka, both of Japan

[21] Appl. No.: 747,965

[22] Filed: Nov. 12, 1996

[30] Foreign Application Priority Data

Nov. 15, 1995 [JP] Japan ................................. 7-321013

[51] Int. Cl.⁶ ........................... G01N 21/00; G01N 1/10
[52] U.S. Cl. ..................... 356/246; 356/440; 356/445
[58] Field of Search ................... 356/246, 39–42, 356/436, 445, 440

[56] References Cited

U.S. PATENT DOCUMENTS

| | | | |
|---|---|---|---|
| 4,302,421 | 11/1981 | Baker | 356/312 |
| 4,979,821 | 12/1990 | Schutt et al. | 356/246 |
| 5,548,393 | 8/1996 | Nozawa et al. | 356/445 |
| 5,608,517 | 3/1997 | Munk | 356/246 |

*Primary Examiner*—Frank G. Font
*Assistant Examiner*—Amanda Merlino
*Attorney, Agent, or Firm*—Sughrue, Mion, Zinn, Macpeak & Seas, PLLC

[57] ABSTRACT

A method and apparatus for detecting presence of liquid in a pathway of known volume feature a molding with a sample receiving port, a pump connection port, at least one sample treating chamber and optionally at least one optical measuring chamber located between the sample receiving port and the pump connection port. The sample receiving port and the treating chambers are connected with each other through a pathway, which passes through the liquid detecting part, that has at least one air hole that is controlled to be in an open or closed state in response to the presence of liquid detected by the liquid detecting part. A sample is quantitatively fed from the sample receiving port into a sample treating chamber. Detection of the liquid involves projecting a light beam at an incident angle in a range of 42° to 62° with respect to the normal upper surface of the pathway; receiving light transmitted through the pathway or reflected from the upper surface of the pathway; and measuring an intensity of the reflected or transmitted light.

11 Claims, 5 Drawing Sheets

TRACE LIQUID DETECTING AND ANALYZING DEVICE

BACKGROUND OF THE INVENTION

1. Field of the Invention

The present invention relates to a method of optically detecting the presence of a trace of liquid, to a detector used therefor and to a trace liquid quantifying instrument using such a method and an device for analyzing a trace of biological liquid sample.

2. Related Art

A disposable dry type analyzing instrument which can be conveniently used for measurement has been desired for analyzing components of a liquid, in particular, a body liquid. It is, in general, preferable to use a body liquid having a quantity as in order to the reduce the burden upon a patient or a sick animal, for analyzing the body fluid; To prevent a biohazard, a method wherein; the body liquid is enclosed in a pathway within an analyzing device, and is displaced by being sucked by a pump in the pathway within which a sample of the body liquid is reacted and measured is also desired. Further, when a sample which contains therein germs or the like, it is particularly desirable to decrease the number of repetitions of pipetting or the like for particularly dripping the sample into an inlet port or the like of the analyzing device.

Conventionally, there have been known, in general, as the method of detecting a liquid, a method which uses electrodes so as to detect a change in conductance through liquid contact with the electrodes, a method in which ultrasonic waves are irradiated so as to detect the presence of liquid, a method in which a change in capacitance or the like depending upon the presence of liquid is detected, and the like. However, since it is preferable for the detection of a trace of a biological liquid sample to use a device which is thin and humetic, since the incorporation of electrodes in such an device is difficult in view of its structure, and since a change in ultrasonic waves and capacitance is slight in the case of detection of liquid which is present in a thin layer, it has been difficult to accurately detect liquid, and to precisely control the quantity of liquid to be fed.

An optical method in which light is transmitted so as to detect a change in transmittance in order to detect the presence of liquid has been used. However, since the change in transmittance is slight in the case of detection of the presence of liquid in a thin layer pathway having a thickness of 0.05 to 0.5 mm, the change can hardly be used as a detection signal.

SUMMARY OF THE INVENTION

The present invention is devised in order to solve the above-mentioned problems inherent to the prior art, and objects of the present invention are to provide a method of detecting a trace of liquid in a thin layer in a analyzing device, an device used therefor, an analyzing device and a trace liquid quantifying instrument.

To this end, according to a first aspect of the present invention, there is provided a method of detecting the presence of liquid in a pathway, comprising the steps of preparing a molding formed therein with a pathway in which a trace of liquid flows while its upper surface is planar, and having an upper part made of transparent materials above the upper surface of the pathway, projecting a beam of light upon the upper surface of the pathway at an incident angle in a range of 42 to 62 deg. with respect to the normal to the upper surface of the pathway, and receiving the transmitted light beam reflected at the upper surface of the pathway, or transmitted through the pathway, and measuring the intensity of the reflected and transmitted light.

According to a second aspect of the present invention, there is provided a liquid detecting device for detecting the presence of liquid, comprising a molding formed therein with a pathway in which a trace of liquid flows having its upper surface which is planar, and an upper part above the upper surface of the pathway, which is made of a transparent material, and an incident surface and an exit surface formed in the external surface of the molding, having an angle in a range between 42 to 62 deg. with respect to the upper surface of the pathway.

According to a third aspect of the present invention, there is provided a body liquid component analyzing device incorporating a at least one of the above-mentioned liquid detecting devices, for measuring optical characteristics of a sample so as to analyze a component of a body liquid. The device comprises a sample receiving port, a pump connecting port, and at least one sample treating chambers and at least one optical measuring chamber, or at least one sample treating/optical measuring chamber, arranged between the sample receiving port and the pump connecting port, the device further comprising, as necessary, a separation part for separating components in the sample, a sample reservoir, and a waste liquid reservoir, the chambers, the separating part and the waste liquid reservoir being connected together through at least one of pathways each having at least one air hole, wherein a sample is distributed among the pathways from the one sample receiving port whereby a plurality of measurements can be carried out for a single sample.

According to a fourth aspect of the present invention, there is provided a trace liquid quantifying instrument attached with the above-mentioned body liquid component analyzing device incorporating the liquid detecting device, comprising an air valve for opening and closing an air hole in the body liquid component analyzing device, a liquid detecting means incorporating a light source from which a light beam is projected, incident upon the incident surface and a light receiver for receiving reflected or transmitted light, and an opening and closing means for opening and closing the air hole in association with detection of liquid.

The present invention will be herein below described in the form of preferred embodiments thereof with reference to the accompanying drawings in which:

PREFERRED EMBODIMENTS OF THE INVENTION

Before detailed description of embodiments of the present invention is made, the principle of incidence and reflection of light upon an optical medium, which is utilized in the present invention, will be described. In general, upon incidence of light from a medium having a refractive index n into a medium having a refractive index $n_0$, the following law of refraction is applicable $n\sin\theta = n_0\sin\theta_0$ where $\theta$ is incident angle, and $\theta_0$ is a refractive angle. In the case of incidence of light into a medium having a refractive index from a medium having a refractive index higher than the former, that is, $n > n_0$, if the incident angle becomes relatively large, $n\sin\theta/n_0 > 1$ is obtained, and accordingly, the above-mentioned law is never satisfied at any value for the refractive index and the light is totally reflected. Such an incident angle that is obtained from $n\sin\theta/n_0 = 1$ is called as a critical angle.

For example, in the case of a glass medium having a refractive index $n/n_0 = 1.52$ with respect to the air, an angle of about 42 deg. can be obtained, which satisfies the above-mentioned condition $n\sin\theta/n_0 = 1$. When the incident angle of light transmitted through the glass medium and impinging upon the interface to the air, is larger than the angle of 42 deg. the light is totally reflected within the glass medium, and never emits into the air. In this case, a value which is obtained by dividing the intensity of the reflected light by the intensity of the incident light gives a reflectance which increases in general as the incident angle increases.

In such a case when air fills in a pathway formed in a glass molding, light is incident upon the pathway at an angle at which the light is totally reflected. However, when water flows in this pathway, the refraction is described by (refractive index of glass =1.52)/(refractive index of water= 1.33)=1.14 while the angle which satisfies $n\sin\theta/n_0 = 1$ becomes about 62 deg., and accordingly, the light incident thereupon is reflected not totally, but partially, with a definite reflectance which has steeply decreased. Accordingly, the presence of liquid in the pathway can be easily detected by detecting a variation of the reflected light.

At least an upper part of a transparent molding above the upper surface of a pathway formed in the molding, is made of glass, acrylic resin, polystyrene resin or the like, having a refractive index of about 1.5. Meanwhile, biological liquid such as plasma to be filled in the pathway has a refractive index of about 1.35. Accordingly, a light beam is projected, incident upon the upper surface of the pathway, at an angle in the range between 42 to 62 deg. with respect to the normal to the upper surface of the pathway, and a change in intensity of reflected light, caused by the presence of the liquid, is measured so as to detect the liquid. In this case, the part below the pathway is not required to be made of a transparent material.

Instead of measuring a change in intensity of the reflected light, a change in intensity of light transmitted through liquid can be measured. In this case, the lower part below the pathway should be made of a transparent material.

An analyzing device having a liquid detecting mechanism for detecting the presence of liquid in a pathway, according to the present invention, comprises a molding formed therein with a flow pathway through which a trace of liquid flows, and made of a transparent material at least in its upper part above the upper surface of the pathway, an incident surface and an exit surface formed in the outer surface of the molding and having an angle in a range between 42 and 62 deg. with respect to the upper surface of the flow pathway, the upper surface of the flow pathway is located, intermediate between the incident surface and the exit surface. In the case of measuring intensity of reflected light above the upper surface of the flow pathway, the incident surface and the exit surface are formed in the same side of the molding, but in the case of measuring an intensity of transmitted light, the incident surface and the exit surface are formed in opposite sides of the molding, respectively.

It is sufficient that the incident surface and the exit surface are formed so that the plane in which a light beam pass has an angle in a range of 42 to 62 deg. with respect to the upper surface of the pathway, and these surfaces can be formed, not only being projected outward from but also caved in the outer surface of the molding. Further, it is preferable to mask parts around the incident surface and the exit surface with black ink or the like in order to eliminate a problem of stray light in the molding.

With the use of the above-mentioned liquid detecting device in a body liquid component analyzing device, it is possible to quantitatively feed a trace of body liquid.

Figure 1:
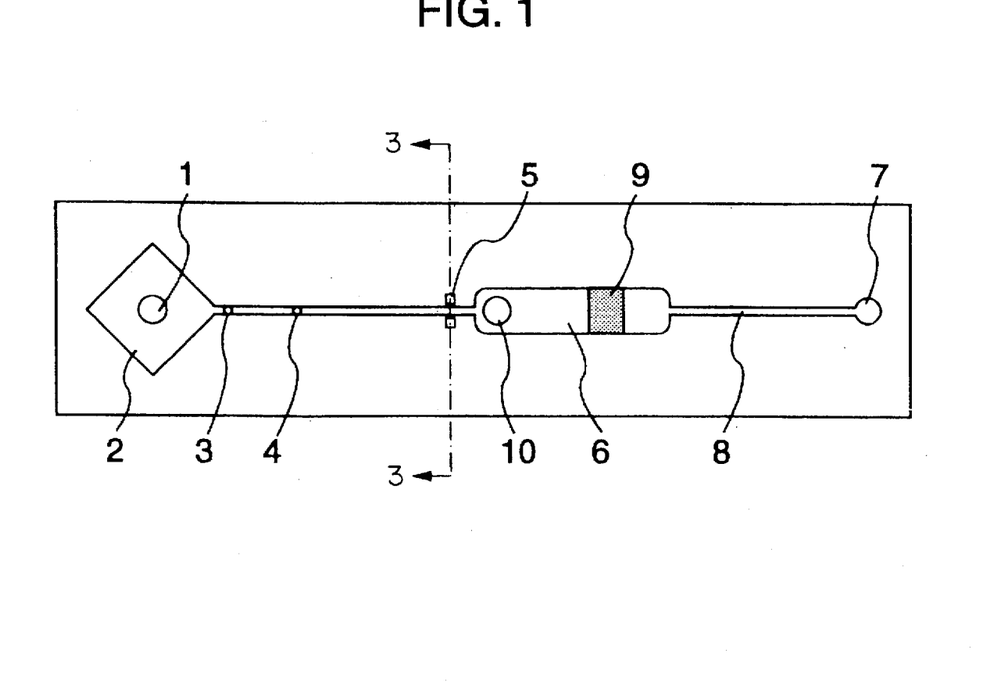
FIG. 1 is a plan view illustrating a body liquid component device in a first embodiment of the present invention.

FIG. 1 is a plan view which shows a body liquid component analyzing device in a first embodiment of the present invention, which will be explained in an example case wherein corpuscles are separated from a sample of whole blood, and plasma is analyzed.

This analyzing device is composed of a sample receiving port 1, a corpuscles separating zone 2, a first air hole 3, a second air hole 4, a liquid detecting part 5, a sample treating and optical measuring chamber 6, a pump connection port 7 and a pathway 8 connecting thereamong. Whole blood which is fed through the sample receiving port 1, and is sucked toward the pump connection port 7, the plasma separated in the blood separating zone 2 is led into the pathway 8. When the plasma which comes to the liquid detecting part 5 is detected, the pump connection port 7 is once opened, and the pathway 8 is depressurized. At this time, the plasma is slightly retracted toward the sample receiving port 1. Then, the first air hole 3 is opened while the plasma is sucked so as to advance the leading end of the plasma toward the liquid detecting part 5. After the first air hole 3 is closed while the second air hole 4 is opened, when the plasma is sucked, only the plasma which is present between the second air hole 4 and the liquid detecting part 5 can be fed into the sample treating and optical measuring chamber 6 for analyzing thereof.

Figure 2:
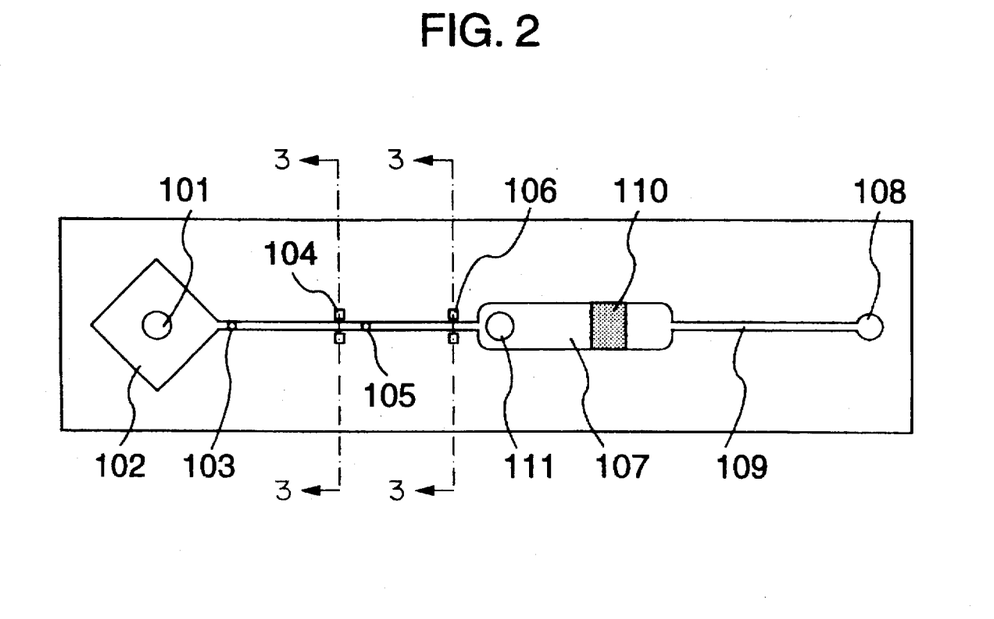
FIG. 2 is a plan view illustrating a body liquid component analyzing device in a variant form of the first embodiment of the present invention.

FIG. 2 is a plan view illustrating a variant form of a body liquid component analyzing device in the first embodiment of the present invention. This body liquid component analyzing device will be explained as an example where a sample of whole blood is used as body liquid and corpuscles are separated from the sample to analyze plasma, as mentioned above. This analyzing device is composed of a sample receiving port 101, a corpuscle separating zone 102, a first air hole 103, a second air hole 105, a first liquid detecting part 104, a second liquid detecting part 106, a sample treating and optical measuring chamber 107, a pump connection port 108 and a pathway 109 connecting thereamong. The whole blood is fed through the sample receiving port 101, and is sucked toward the pump connection port 108. Accordingly, the plasma separated in the corpuscle separating zone 102 is led into the pathway 109. When the plasma reaching the first liquid detecting part 104 is detected, the second air hole 105 is once opened so that the depressurization in the pathway 109 is released. At this time, the plasma in the flow pathway 109 is slightly retracted toward the sample receiving port 101. Then, the first air hole 103 is opened but the second air hole 105 is closed while suction is effected through the pathway 109, and accordingly, the leading end of the plasma is shifted to the second liquid detecting part 106. The first air hole 103 is closed but the second air hole 105 is opened while suction is effected through the pathway 109, the plasma extending between the second air hole 105 and the second liquid detecting part 106 is shifted into the sample treating and optical measuring chamber 107 for analyzing the plasma.

Figure 3:
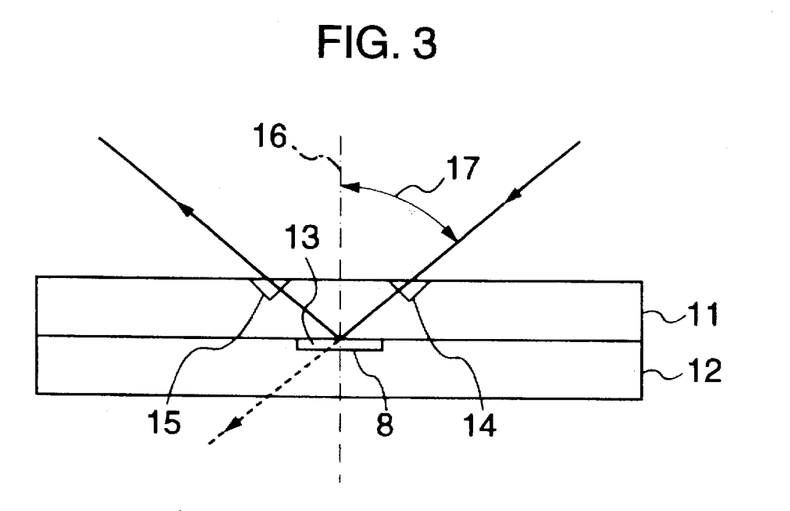
FIG. 3 is a sectional view along line A—A in FIG. 1 or FIG. 2.

FIG. 3 is a sectional view which shows the liquid detecting part 5, 104, 106 in the body liquid analyzing device shown in FIGS. 1 and 2. In this case, the molding is composed of an upper plate 11 and a lower plate 12 which are made of a transparent material, and a pathway 8 is formed in the lower plate 12 while an incident surface 14 and an exit surface 15 are formed in the upper plate 11. A light beam having an incident angle 17 in a range from 42 to 62 deg. with respect to the normal 16 to the upper surface of the pathway 8, passes, perpendicular to the incident surface 14, then is reflected at the upper surface 13 of the pathway 8, and thereafter, it passes, perpendicular to the exit surface 15, so as to be measured by a light receiver (which is not shown). Thus, whether the liquid is present in the pathway 8 or not can be detected in accordance with the thus measured value.

Figure 4:
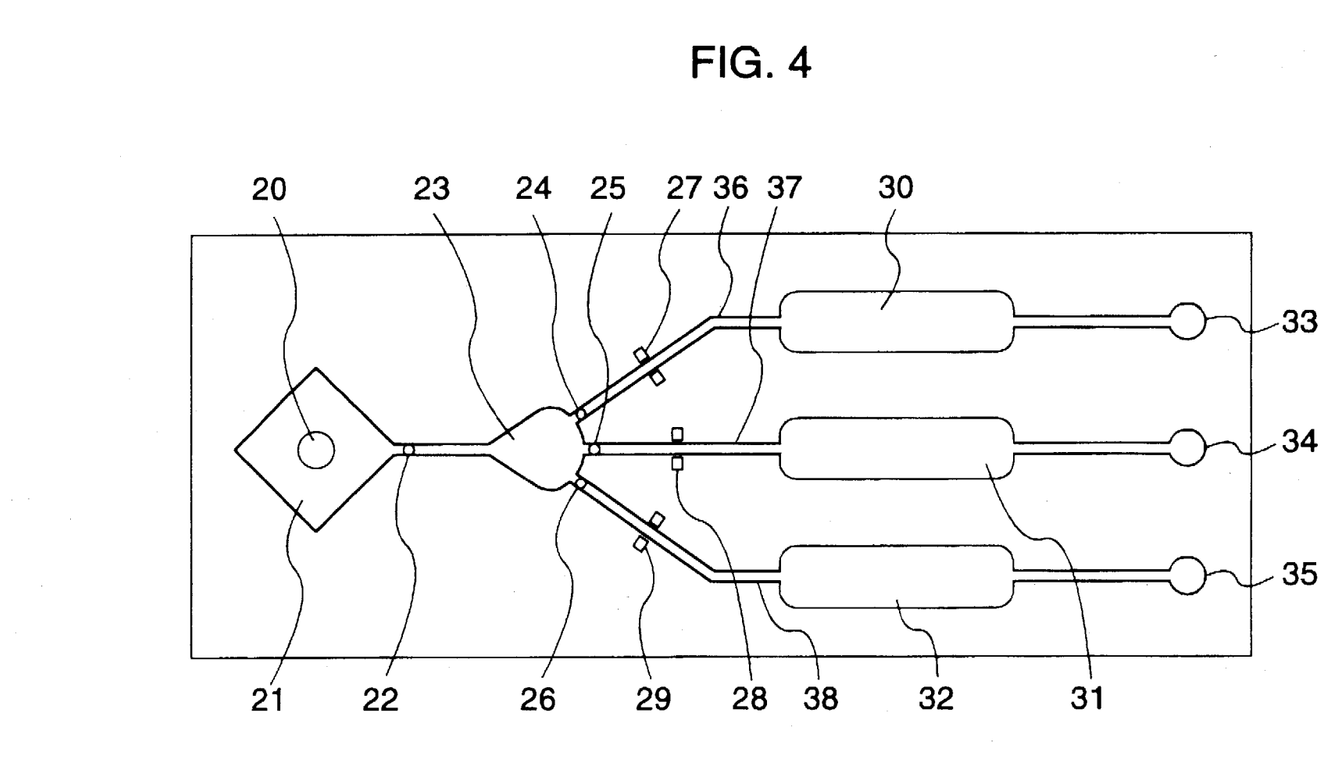
FIG. 4 is a plan view illustrating a body liquid component analyzing device having a plurality of pathway in a second embodiment of the present invention.

FIG. 4 shows a body liquid component analyzing device, in a second embodiment of the present invention, incorporating liquid detecting parts as mentioned above. In this embodiment, a sample reservoir, is provided, and three branch pathways each incorporating an air hole, branch from the sample reservoir. In this embodiment, explanation will be made in the case of using a sample of whole blood.

The whole blood fed through a sample receiving port 20 is led by suction from a third pump connection port 35 into a corpuscle separating zone 21 in which the whole blood is separated into the plasma and the corpuscles. The plasma is filled in the sample reservoir 23, and thereafter, it comes to a third liquid detecting part 29. At this time, the third pump connection port 35 is once opened so that the pressure is returned to the atmospheric pressure, and then, the first air hole 22 is opened. The plasma is sucked through first, second and third branch pathways 36, 37, 38 which are incorporated therein with second, third and fourth air holes 24, 25, 26 by pumps connected to the branch pathways while the second, third and fourth air holes 24, 25, 26 are closed so as to introduce the plasma into the branch pathways. Accordingly, the plasma flows through these three branch pathways, and when the presence of the plasma in the branch pathways is detected at first, second, and third liquid detecting parts 27, 28, 29, the second, third and fourth air holes 24, 25, 26 are opened, and accordingly, plasma in predetermined quantities is metered in the respective branch pathways. Thereafter, the plasma is preprocessed, reacted, optically measured and so forth, as necessary, in first, second and third sample treating and optical measuring chambers 30, 31, 32 so as to carry out analysis for various components of the body liquid.

Explanation will be hereinbelow made of a specific process of separating and extracting the plasma with the use of the body liquid component analyzing device shown in FIG. 4. At step 1, in a condition in which the first and second suction pumps connected respectively to the first and second pump connection ports 33, 34 are deenergized while the third suction pump connected to the third pump connection port 35 is energized, and the first, second, third and fourth air holes 22, 24, 25, 26 are closed, the liquid flows to the third liquid detecting part 29 under suction through the third pump connection port 35, and accordingly, the liquid is detected in the liquid detecting part 29. In response to this detection, the third pump connection port 35 is isolated from the third suction pump, and is opened to the atmosphere while the first air hole 22 is opened so that the atmospheric pressure is effected in the third pathway 38. At step 2, in such a condition in which the first and second pumps connected to the first and second pump connection ports 33, 34 are deenergized while the third suction pump is connected to the third pump connection port 35 and is energized, the first air hole 22 is opened so that the leading end of the liquid comes to the third liquid detecting part 29. At step 3, the first air hole 22 is closed when the liquid is detected in the third liquid detecting part 29, and the fourth air hole 26 is opened. Accordingly, the liquid in the part extending between the fourth air hole 26 to the third liquid detecting part 29 flows into the third pathway 38 communicated with the third sample treating and optical measuring chamber 32, that is, a predetermined quantity of the liquid is led into the third pathway 38 up to a position just before the third sample treating and optical measuring chamber 32 (when the third liquid detecting part 29 does not detects the liquid any more, the third suction pump is deenergized). At step 4, in such a condition in which the fourth air hole 26 is closed, and the first suction pump connected to the first pump connection port 33 and the third suction pump connected to the third pump connection port 35 are deenergized while the second suction pump connected to the second pump connection port 34 is energized, the first air hole 22 is opened so that the leading end of the liquid comes to the second liquid detecting part 28. At step 5, when the liquid is detected in the second liquid detecting part 28, the first air hole 22 is closed while the third air hole 25 is opened so that the liquid in the part extending from the third air hole 25 to the second liquid detecting part 28 flows into the second pathway 37 up to a position just before the second sample treating and optical measuring chamber 31 (the second suction pump is deenergized when the second liquid detecting part 28 does not detect the liquid any more). At step 6, in such a condition that the third air hole 25 is closed while the second and third suction pumps connected respectively to the second and third pump connection ports 34, 35, are deenergized while the first suction pump is connected to the first pump connection port 33 and is energized, the first air hole 22 is opened so that the leading end of the liquid comes to the first liquid detecting part 27. At step 7, when the liquid is detected by the first liquid detecting part 27, the first air hole 22 is closed while the second air hole 24 is opened, and accordingly, the liquid in the part extending from the second air hole 24 to the first liquid detecting part 27 flows into the first pathway 36 up to a position just before the first sample treating and optical measuring chamber 30 (when the first liquid detecting part 27 does not detect the liquid any more, the first suction pump is deenergized). At step 8, the first to third pumps are connected to the first to third pump connection ports 33, 34, 35, respectively, and are energized while the first hole 22 is closed and the second, third and fourth air holes 24, 25, 26 are opened, and accordingly, the liquid in the three pathways 33, 34, 35 are led through the first to third sample treating and optical measuring chambers 30, 31, 32 so that the liquid is reacted and optically measured.

It is noted that step 1 is adapted to introduce the plasma into the pathways, and the liquid may be sucked through any one of the first to third pump connection ports 33, 34, 35.

Figure 5:
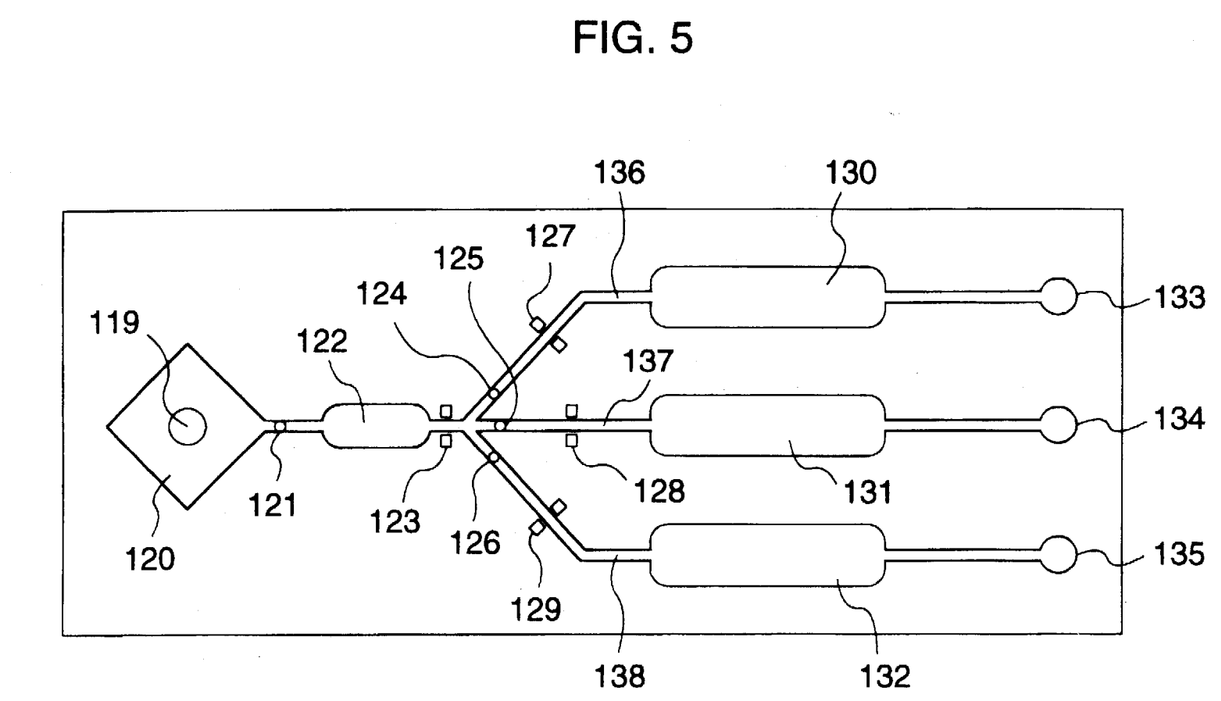
FIG. 5 is a plan view illustrating a body liquid component analyzing device in a variant form of the second embodiment of the present invention.

Referring to FIG. 5 which is a plan view, a body liquid component analyzing device incorporating body liquid detecting parts as mentioned above in a variant form of the second embodiment of the present invention will be hereinbelow explained. In this variant form, similar to the body liquid component analyzing device shown in FIG. 4, a sample reservoir is provided, and three pathways each having air hole, branch from the sample reservoir. Further, explanation will be made in the case of using a sample of whole blood.

The whole blood fed through a sample receiving port 119 is led by suction from a third pump connection port 135 into a corpuscle separating zone 120 in which the whole blood is separated into the plasma and the corpuscles. The plasma is filled in the sample reservoir 122, and thereafter, it comes to a first liquid detecting part 123. At this time, first, second and third air holes 124, 125, 126 formed respectively in first, second and third pathways 136, 137, 138 are once opened so that pressures in the pathways are returned to the atmospheric pressure, then the first air hole 121 is opened. Next, the second, third and fourth air holes 124, 125, 126 are closed, and suction is effected by the pumps in order to introduce the plasma into the branch pathways 136, 137, 138. Accordingly, the plasma flows through the first, second and third branch pathways 136, 137, 138, and is detected at, second, third and fourth liquid detecting parts 127, 128, 129. At this time, the first air hole 121 is closed while the second, third and fourth air holes 124, 125, 126 are opened, and accordingly, plasma in predetermined quantities is metered in the respective branch pathways 136, 137, 138. Thereafter, the plasma is preprocessed, reacted, optically measured and so forth, as necessary, in first, second and third sample treating and optical measuring chambers 130, 131, 132 so as to carry out analysis for various components of the body liquid.

Explanation will be hereinbelow made of a specific process of separating and extracting the plasma with the use of the body liquid component analyzing device shown in FIG. 5. At step 1, in a condition in which the first and second suction pumps connected respectively to the first and second pump connection ports 133, 134 are deenergized while the third suction pump connected to the third pump connection port 135 is energized, and the first, second, third and fourth air holes 121, 124, 125, 126 are closed, the liquid flows to the first liquid detecting part 123 under suction through the third pump connection port 1357 and accordingly, the liquid is detected in the first liquid detecting part 123. In response to this detection, the second, third and fourth air holes 124, 125, 126 are opened so as to effect the atmospheric pressure in the pathways. At step 2, in such a condition that the first air hole 121 is opened, and first and second pumps connected to the first and second pump connection ports 133, 134 but are deenergized while the third suction pump is connected to the third pump connection port 135 and is energized, the second, third and fourth air holes 124, 125, 126 are closed so that the leading end of the liquid comes to the fourth liquid detecting part 129. At step 3, the first air hole 121 is closed when the liquid is detected in the fourth liquid detecting part 129., and the fourth air hole 126 is opened. Accordingly, the liquid in the part extending between the fourth air hole 126 to the fourth liquid detecting part 129 flows into the third pathway 138 communicated with the third sample treating and optical measuring chamber 132, that is, a predetermined quantity of the liquid is led into the third pathway 138 up to a position just before the third sample treating and optical measuring chamber 132. At step 4, in such a condition that the fourth air hole 126 is closed, and the first suction pump connected to the first pump connection port 133 and the third suction pump connected to the third pump connection port 135 are deenergized while the second suction pump connected to the second pump connection port 134 is energized, the first air hole 121 is opened so that the leading end of the liquid comes to the third liquid detecting part 128. At step 5, when the liquid is detected in the third liquid detecting part 128, the first air hole 121 is closed while the third air hole 125 is opened so that the liquid in the part extending from the third air hole 125 to the third liquid detecting part 128 flows into the second pathway 137 up to a position just before the second sample treating and optical measuring chamber 131. At step 6, in such a condition that the third air hole 125 is closed while the second and third suction pumps connected respectively to the second and third pump connection ports 134, 135, are deenergized while the first suction pump is connected to the first pump connection port 133 and is energized, the first air hole 121 is opened so that the leading end of the liquid comes to the second liquid detecting part 127. At step 7, when the liquid is detected by the second liquid detecting part 127, the first air hole 121 is closed while the second air hole 124 is opened, and accordingly, the liquid in the part extending from the second air hole 124 to the second liquid detecting part 127 flows into the first pathway 136 up to a position just before the first sample treating and optical measuring chamber 130. At step 8, the first, second and third pumps are connected to the first, second and third pump connection ports 133, 134, 135, respectively, and are all energized while the second, third and fourth air holes 124, 125, 126 are opened, and accordingly, the liquid in the three pathways 136, 137, 138 are led through the first to third sample treating and optical measuring chambers 130, 131, 132 so that the liquid is reacted and optically measured.

It is noted that step 1 is adapted to introduce the plasma into the pathways, and the liquid may be sucked through any one of the first to third pump connection ports 133, 134, 135 or any combination thereof.

REFERENCE EXAMPLES

Explanation will be made of reference examples in which a liquid detecting method according to the present invention is used.

Reference Example 1:

Comparison between Transmission and Reflection of Light at Thin Layer Cell

Figure 6:
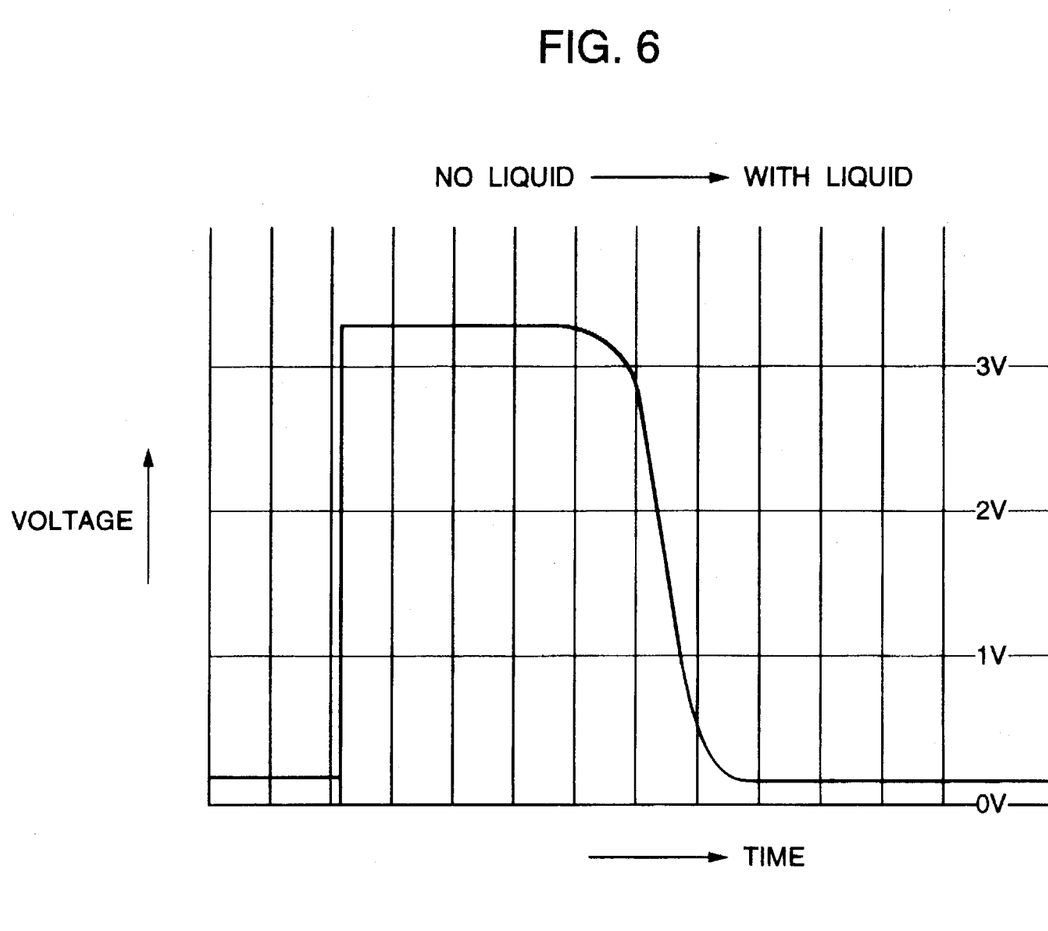
FIG. 6 is a graph showing voltage variation upon detection of liquid.

Liquid was led through a pathway having a depth of 0.1 mm and a width of 1.0 mm and formed in a plate which is held between two polystyrene resin plates having a thickness of 1.5 mm, and a change in light quantity at a light receiver in the liquid detecting part was measured. The incident surface was formed in the polystyrene resin plate on the light projection side so that the incident angle of the light beam onto the upper surface of the pathway became 52 deg. The exit surface was formed on the light receiver side so that the reflective angle of a reflected light beam received from the upper surface of the pathway becomes an angle of 52 deg. Both incident surface and exit surface have a length of 1 mm and a width of 0.6 mm. A light emitting diode L630 manufactured by Epitex Co., Ltd. was used as a light source, and a phototransistor TPS613C manufactured by Toshiba Co., was used as a light receiver. The flow of the liquid in the pathway was controlled so that the flow rate of the liquid was set to 0.3 μl/sec. FIG. 6 shows the output of the light receiver which was converted and recorded on the recorder. Time elapse is taken on the X-axis, having a unit scale of 1 sec.

As understood from FIG. 6, the voltage is 3.25 V when no liquid flows but it abruptly drops when the liquid flows in the pathway, and it comes down to 0.19 V when the liquid is filled in the pathway. That is, this fact exhibits such that the quantity of reflected light at the upper surface of the pathway toward the light receiver decreases as the liquid enters the flow pathway, and substantially no reflected light is present when the liquid is filled in the pathway.

Accordingly, by setting the level of detection of the liquid to, for example, 1 V, a value less than 1 indicates that the liquid is filled in the light detecting part, but a value greater than 1 V indicates that no liquid is present in the light detecting part. Further, by setting the level of detection of the liquid at two points such as 1 V and 2 V, any one of a condition in which no liquid is filled in the liquid detecting part, a condition in which the liquid just comes into the liquid detecting part and a condition in which the liquid was filled in the liquid detecting part can be detected.

Reference Example 2:

Measurement by Analyzing Device having Plural Pathways

With the use of the body liquid component analyzing device according to the present invention, as shown in FIG. 4, the separation and quantification of a sample was carried out with the use of the operation steps in the second embodiment. A membrane filter having a length of 10 mm and width of 10 mm and an asymmetric pore diameter was attached to the corpuscle separating part 21 by retaining the membrane at its peripheral part so as to prevent occurrence of leakage of the corpuscles from the periphery of the membrane. 0.5 g/l (0.05% Triton X-405 water solution) 1.5 µl of food dye blue No.1 as a reagent is dripped into each of the first to third sample treating and optical measuring chambers 30, 31, 32, and was then dried.

The pathway had a height of 0.1 mm and a width of 1 mm, a sample reservoir 23 had a volume of 5 µl, the sample treating and optical measuring chambers had a width of 3 mm, and each of the distances between the first to the third air holes 24, 25, 26 and the first to third liquid detecting parts 27, 28, 29 was set to 15 mm.

20 µl of the blood was dripped into the sample receiving port 20, suction was made through the third pump connection port 35 in a condition where the third pump connection port 35 was connected to the third pump while; all other ports and air holes were closed, (step 1), and accordingly, the internal pressure dropped. Thus, the plasma filled in the pathway and the sample reservoir 23 successively, and arrived at the first to third liquid detecting parts 27, 28, 29. The operation steps 2 to 8 were carried out so as to dissolve the blue food dye in the sample treating and optical measuring chambers 30, 31, 32, and a light absorbance of the blue food dye was measured with the light having a wavelength of 630 nm. Each of the air holes was opened and closed by a rubber plate which was driven by a solenoid, and a mechanism for opening the pathway to the atmosphere was provided between the pump connection port and the pump. The same experiment was repeated by five times. The results of the experiments are shown in Table 1.

TABLE 1

Measurement of Light Absorbance with Use of Analyzing Device having Plural Pathways

| | Light Absorbance | | |
| --- | --- | --- | --- |
| | #1Processing Camber | #2Processing Camber | #3Processing Camber |
| 1 | 0.842 | 0.841 | 0.842 |
| 2 | 0.843 | 0.842 | 0.844 |

TABLE 1-continued

Measurement of Light Absorbance with Use of Analyzing Device having Plural Pathways

| | Light Absorbance | | |
| --- | --- | --- | --- |
| | #1Processing Camber | #2Processing Camber | #3Processing Camber |
| 3 | 0.861 | 0.860 | 0.862 |
| 4 | 0.840 | 0.838 | 0.841 |
| 5 | 0.842 | 0.840 | 0.852 |

Referring to Table 1, during each of the experiments, the concentrations of the samples in the 5 first to third sample processing chambers 30, 31, 32 were substantially identical with one another. It is found that the sample could be fed at a uniform rate through the first to third pathways 36, 37, 38.

Comparison Example:

Liquid Detection in Vertical Direction

Experiment similar to that in the first reference example was carried out by projecting a light beam, perpendicular to the pathway, and by measuring the light beam transmitted through the pathway. As a result, the voltage of the light receiver did not change and was held at 3.2 V even though the liquid was filled in the light detecting part, and accordingly, no signal which can detect the presence of the liquid could not be obtained. This means that the light beam incident upon the liquid perpendicular thereto is transmitted directly therethrough without absorption, and accordingly, the light quantity which can be received by the light receiver does not change substantially.

According to the present invention, a method of detecting a trace of liquid in a thin layer within an analyzing device, an device used in the method, an analyzing device and a trace liquid quantifying instrument can be provided.

What is claimed is:

1. A liquid detecting method for detecting the presence of liquid in a pathway, comprising the steps of:

feeding a liquid to be detected to a sample receiving reservoir that is connected to a pathway that is formed in a molding and that includes a liquid detecting part, wherein said pathway has at least one air hole that is controlled to be in an open or closed state in response to the presence of liquid detected in the liquid detecting part, so that said liquid is quantitatively metered from said sample receiving reservoir through said liquid detecting part, and wherein said pathway has an an upper surface which is planar, and wherein said molding is made of a transparent material at least in a part above the upper surface of said pathway;

projecting a light beam at an incident angle in a range of 42° to 62° with respect to the normal to the upper surface of the said pathway;

receiving light transmitted through said pathway or reflected from the upper surface of said pathway;

measuring an intensity of the reflected or transmitted light; and observing substantially no reflected light as indication that liquid is passing a beam of said light at the upper surface of said pathway.

2. An analyzing device according to claim 1, wherein the molding part is made of a transparent material at least in an upper part above the upper surface of said pathway.

3. An analyzing device as set forth in claim 2, wherein said incident and exit surfaces are formed in an external surface of said molding on the same side, the upper surface of said pathway is located, intermediate between said incident and exit surfaces, and a reflected light beam at the upper surface of said pathway is transmitted through said exit surface.

4. An analyzing device as set forth in claim 2, wherein said incident and exit surfaces are formed in an external surface of said molding on opposite sides, the upper surface of said pathway is located, intermediate between said incident and exit surfaces, and transmitted light through the upper surface of said pathway is transmitted through said exit surface.

5. An analyzing device for analyzing a component of a sample of body liquid by measuring optical characteristic thereof, comprising:

a molding part with a pathway formed therein in which a trace of liquid flows having its upper surface which is planar;

a liquid detecting part having an incident surface and an exit surface formed in an external surface of said molding part and having an angle in a range from 42° to 62° with respect to the upper surface of the flow pathway, for detecting the presence of the liquid;

a sample receiving port;

a pump connection port;

at least one sample treating chamber and at least one optical measuring chamber located between said sample receiving port and said pump connection port; and said sample receiving port and said at least one sample treating chamber are connected with each other through a pathway which passes through said liquid detecting part, having at least one air hole, that is controlled to be in an open or closed state in response to the presence of liquid detected by the liquid detecting part, so that a sample is quantitatively fed from said sample receiving port into said at least one sample treating chambers.

6. An analyzing device as set forth in claim 5, wherein said incident and exit surfaces are formed in the external surface of said molding on the same side, the upper surface of said pathway is located, intermediate between said incident and exit surfaces, and reflected light at the upper surface of said pathway is transmitted through said exit surface.

7. An analyzing device as set forth in claim 5, wherein said incident and exit surfaces are formed in the external surface of said molding on opposite sides, the upper surface of said pathway is located, intermediate between said incident and exit surfaces, and transmitted light at the upper surface of said pathway is transmitted through said exit surface.

8. An analyzing device as set forth in claim 5, wherein said at least one sample treating chamber and said at least one optical measuring chamber are integrally incorporated with each other.

9. An analyzing device as set forth in claim 5, wherein a sample reservoir is provided in said pathway, upstream said at least one of air hole.

10. An analyzing device as set forth in claim 5, wherein said pathway includes a plurality of branch pathways branching downstream of said sample reservoir, each of said branch pathways passes through a liquid detecting part, and is then connected to a sample treating chamber, and each of said branch pathways is formed therein with an air hole which is opened and closed in association with detection of said liquid by an associated liquid detecting part, whereby the sample is quantitatively fed into said plurality of branch pathways, respectively.

11. A trace liquid quantifying instrument used in a liquid analyzing apparatus having a sample receiving port, a sample treating chamber and a pathway connecting between the sample receiving port and the sample treating chamber, comprising:

an air hole formed in said pathway;

a means for opening and closing said air hole;

a means provided between said air hole and said sample treating chamber, for optically detecting the liquid, said pathway passing through said detecting means;

a control means for operating said opening and closing means in association with detection of said liquid detecting means.

* * * * *

UNITED STATES PATENT AND TRADEMARK OFFICE
CERTIFICATE OF CORRECTION

PATENT NO. : 5,764,356

DATED : June 9, 1998

INVENTOR(S) : Kenichi Iwase, et al

It is certified that error appears in the above-identified patent and that said Letters Patent is hereby corrected as shown below:

Column 2 line 53, change "A-A" to --3-3--.

Signed and Sealed this

Ninth Day of February, 1999

Attest:

Acting Commissioner of Patents and Trademarks

Attesting Officer